(12) United States Patent
Liao et al.

(10) Patent No.: US 11,583,855 B2
(45) Date of Patent: Feb. 21, 2023

(54) MICROFLUIDIC STRUCTURE, MICROFLUIDIC CHIP AND DETECTION METHOD

(71) Applicants: Beijing BOE Sensor Technology Co., Ltd., Beijing (CN); BOE Technology Group Co., Ltd., Beijing (CN)

(72) Inventors: Hui Liao, Beijing (CN); Yingying Zhao, Beijing (CN); Bolin Fan, Beijing (CN); Wenliang Yao, Beijing (CN); Nan Zhao, Beijing (CN); Le Gu, Beijing (CN); Yongjia Gao, Beijing (CN)

(73) Assignees: Beijing BOE Sensor Technology Co., Ltd., Beijing (CN); BOE Technology Group Co., Ltd., Beijing (CN)

(*) Notice: Subject to any disclaimer, the term of this patent is extended or adjusted under 35 U.S.C. 154(b) by 197 days.

(21) Appl. No.: 17/186,186

(22) Filed: Feb. 26, 2021

(65) Prior Publication Data

US 2021/0268499 A1 Sep. 2, 2021

(30) Foreign Application Priority Data

Feb. 28, 2020 (CN) .......................... 202010128219.5

(51) Int. Cl.
*B01L 3/00* (2006.01)
*G01N 27/22* (2006.01)
*G01N 33/577* (2006.01)

(52) U.S. Cl.
CPC ...... *B01L 3/502715* (2013.01); *G01N 27/226* (2013.01); *G01N 33/577* (2013.01); *B01L 13/00* (2019.08); *B01L 2300/0636* (2013.01); *B01L 2300/0645* (2013.01); *B01L 2400/0415* (2013.01); *G01N 2458/30* (2013.01)

(58) Field of Classification Search
CPC ......... B01L 3/502715; B01L 3/502792; B01L 3/502761; B01L 13/00; B01L 2300/0636; B01L 2300/0645; B01L 2300/0819; B01L 2400/0415; B01L 2400/0427; B01L 2200/16; G01N 27/226; G01N 33/577; G01N 33/5438; G01N 33/558; G01N 2458/30
See application file for complete search history.

(56) References Cited

U.S. PATENT DOCUMENTS

2014/0151232 A1* 6/2014 Hadwen ................. G09G 3/348
204/547

* cited by examiner

*Primary Examiner* — Jennifer Wecker
*Assistant Examiner* — Alea N. Martin
(74) *Attorney, Agent, or Firm* — ArentFox Schiff LLP; Michael Fainberg (57) ABSTRACT

The present disclosure discloses a microfluidic structure, a microfluidic chip and a detection method. The microfluidic structure includes: a first base substrate and a second base substrate opposite to each other, an antibody area located between the first base substrate and the second base substrate and storing an enzyme-labeled first antibody, a cleaning area storing cleaning liquid, a signal substrate area storing a signal substrate solution and a detection area with a second antibody and an ion sensitive film fixed thereon, wherein all channel areas from the antibody area, the cleaning area and the signal substrate area to the detection area each have a driving electrode structure driving liquid drops to move; and the detection area has a thin film transistor connected with the ion sensitive film.

14 Claims, 6 Drawing Sheets

MICROFLUIDIC STRUCTURE, MICROFLUIDIC CHIP AND DETECTION METHOD

This application claims priority to Chinese Patent Application No. 202010128219.5, filed on Feb. 28, 2020, which is hereby incorporated by reference in its entirety.

FIELD

The present disclosure relates to the field of microfluidic chips, in particular to a microfluidic structure, a microfluidic chip and a detection method.

BACKGROUND

Acute myocardial infarction (AMI) has been one of main diseases which do harm to human health. In recent years, along with increasing study on this disease, cardiac markers in blood samples can be detected so as to prevent as soon as possible or rapidly diagnose this disease, thereby preventing disability, mortality and other consequences caused by myocardial infarction to the maximum degree. The cardiac markers can sensitively and specifically reflect myocardial damage and its severity in circulating blood so as to serve as markers of screening, diagnosis, prognosis evaluation and treatment effect follow-up visit of myocardial damage.

The cardiac markers mainly include cardiac troponin (cTnI), myoglobin, creatine kinase isoenzyme (CK-MB), N-terminal pro-brain natriuretic peptide (NT-proBNP), B-type natriuretic peptide (BNP), etc.

SUMMARY

The present disclosure provides a microfluidic structure, a microfluidic chip and a detection method.

An embodiment of the present disclosure provides a microfluidic structure, including: a first base substrate and a second base substrate opposite to each other, an antibody area located between the first base substrate and the second base substrate and storing an enzyme-labeled first antibody, a cleaning area storing cleaning liquid, a signal substrate area storing a signal substrate solution and a detection area with a second antibody and an ion sensitive film fixed thereon. The enzyme-labeled first antibody includes a first antibody and an enzyme attached to the first antibody, the first antibody is an antibody matched with a to-be-detected antigen, and the second antibody is an antibody matched with the first antibody.

All channel areas from the antibody area, the cleaning area and the signal substrate area to the detection area each have a driving electrode structure driving liquid drops to move.

The detection area has a thin film transistor connected with the ion sensitive film.

In some embodiments, the ion sensitive film and the second antibody are located on the same layer. The ion sensitive film has a hollow-out area, and the second antibody is located in the hollow-out area.

In some embodiments, the thin film transistor includes a source electrode and a drain electrode located on the first base substrate, an active layer located on one face of the source electrode and one face of the drain electrode facing the second base substrate, a gate electrode insulation layer located on one face of the active layer facing the second base substrate and a gate electrode located on one face of the gate electrode insulation layer facing the second base substrate.

The ion sensitive film covers one face of the gate electrode facing the second base substrate.

In some embodiments, the driving electrode structure includes a plurality of first electrodes located on the first base substrate at intervals and a common electrode located on the second base substrate.

In some embodiments, each of the channel areas further includes a first hydrophobic layer located on one face of the first electrodes facing the second base substrate, and a second hydrophobic layer located on one face of the common electrode facing the first base substrate.

In some embodiments, each of the channel areas further includes a dielectric layer located between the first electrodes and the first hydrophobic layer.

In some embodiments, the microfluidic structure further includes: a sample area located between the first base substrate and the second base substrate and storing the to-be-detected antigen. A channel area from the sample area to the detection area also has a driving electrode structure driving the liquid drops to move.

In some embodiments, the microfluidic structure further includes: a waste liquid area located between the first base substrate and the second base substrate.

A channel area from the detection area to the waste liquid area also has a driving electrode structure driving the liquid drops to move.

In some embodiments, the enzyme includes: alkaline phosphatase or horse radish peroxidase.

In some embodiments, a signal substrate includes: phospholipid aminobenzoate or 2-phosphate ascorbate.

An embodiment of the present disclosure further provides a microfluidic chip, including a plurality of microfluidic structures provided by the embodiments of the present disclosure.

An embodiment of the present disclosure further provides a detection method driving the microfluidic structure provided by the embodiments of the present disclosure, including: combining the to-be-detected antigen with the enzyme-labeled first antibody to form antigen/enzyme-labeled antibody mixed liquid drops by adding the to-be-detected antigen into the antibody area; driving the antigen/enzyme-labeled antibody mixed liquid drops to move from the antibody area to the detection area by sequentially loading a voltage to the driving electrode structure from the antibody area to the detection area, and forming antigen/antibody sandwich composite liquid drops by combining the antigen/enzyme-labeled antibody mixed liquid drops with the second antibody; after a first duration, driving cleaning liquid drops in the cleaning area to move to the detection area to take away a non-combined reactant by sequentially loading a voltage to the driving electrode structure from the cleaning area to the detection area; after a second duration, driving signal substrate liquid drops in the signal substrate area to move to the detection area and make a signal substrate form ions under the action of the enzyme and make the ion sensitive film produce inductive charges under the action of the ions by sequentially loading a voltage to the driving electrode structure from the signal substrate area to the detection area; and determining a content of the to-be-detected antigen according to an electrical signal generated by the thin film transistor under the action of the inductive charges.

In some embodiments, adding the to-be-detected antigen to the antibody area includes: adding the to-be-detected antigen to a sample area; and driving liquid drops containing the to-be-detected antigen in the sample area to move to the antibody area by sequentially loading a voltage to a driving electrode structure from the sample area to the antibody area.

In some embodiments, before sequentially loading a voltage to a driving electrode structure from the signal substrate area to the detection area, the detection method further includes: driving the non-combined reactant to move to the waste liquid area by sequentially loading a voltage of a driving electrode structure from the detection area to a waste liquid area.

DETAILED DESCRIPTION OF THE EMBODIMENTS

In order to make objectives, technical solutions and advantages of the embodiments of the present disclosure clearer, the technical solutions of the embodiments of the present disclosure will be clearly and completely described below in combination with the accompanying drawings of the embodiments of the present disclosure. Apparently, the described embodiments are part of the embodiments of the present disclosure instead of all embodiments. On the basis of the described embodiments of the present disclosure, all of the other embodiments obtained by those ordinarily skilled in the art without creative work fall in the protection scope of the present disclosure.

Unless otherwise defined, technical terms or scientific terms used in the present disclosure should have common meanings understood by those ordinarily skilled in the art of the present disclosure. "First", "second" and similar words used in the present disclosure are only used for distinguishing different compositions rather than represent any sequence, quantity or significance. "Comprise" or "include" and other similar words denote that an element or an item appearing before the words contains elements or items and their equivalents listed after the words without excluding other elements or items. "Joint" or "connection" and other similar words may include electrical connection despite of being direct or indirect instead of being limited to physical connection or mechanical connection. Words like "Up", "down", "left" and "right" are only used for representing a relative position relation, and when an absolute position of a described object changes, the relative position relation may change correspondingly as well.

In order to keep the description of the embodiments of the present disclosure clear and simple, the detailed descriptions of known functions and known parts are omitted in the present disclosure.

Existing detection of cardiac markers mainly includes a test strip based on enzyme immunoassay and a chemiluminescence apparatus. The enzyme immunoassay test strip has a main defect of large batch difference with a variable coefficient being generally 15% to 30%. The chemiluminescence apparatus is usually combined with a magnetic bead capture technology, a magnetic control module needs to be added, and part of magnetic beads may be washed away along with a reagent; and besides, the chemiluminescence apparatus needs an external integrated signal detector such as a charge-coupled device (CCD) or a photomultiplier tube (PMT), and background light noise interference may occur. Accordingly the chemiluminescence apparatus for detection of the cardiac markers is large in size and difficult to carry along and is limited in bedside detection, emergency ambulance detection and household detection. Namely, problems that detection is inaccurate, detection equipment is large in size, and the equipment is expensive and inconvenient to carry along lie in detection of antigens including the cardiac markers and the like in the prior art.

Figure 1:
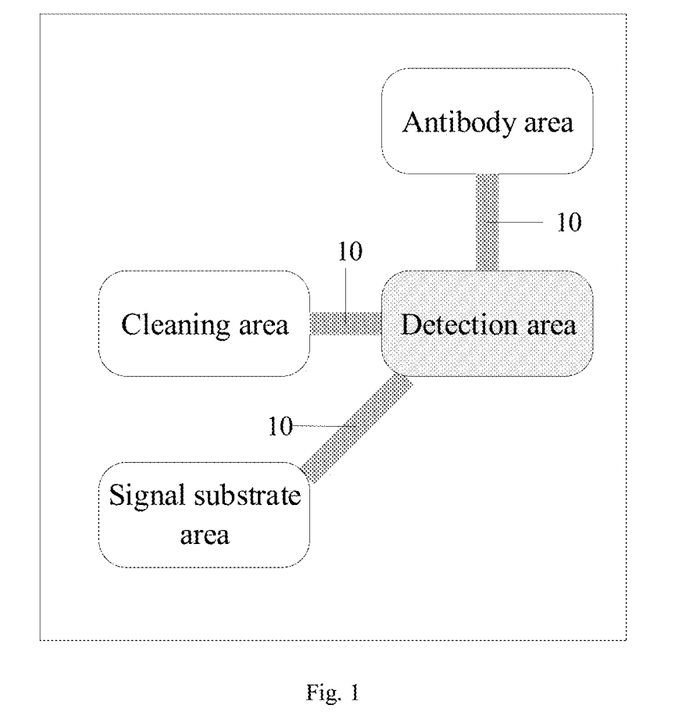
FIG. 1 is a schematic top view of a microfluidic structure provided by an embodiment of the present disclosure.
Figure 2:
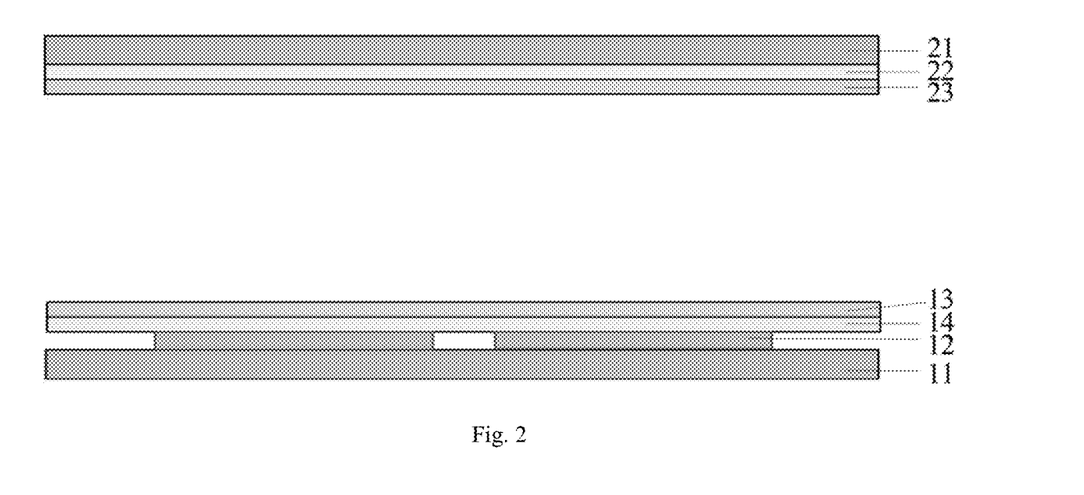
FIG. 2 is a schematic sectional view of a microfluidic structure in channel areas provided by an embodiment of the present disclosure.
Figure 3:
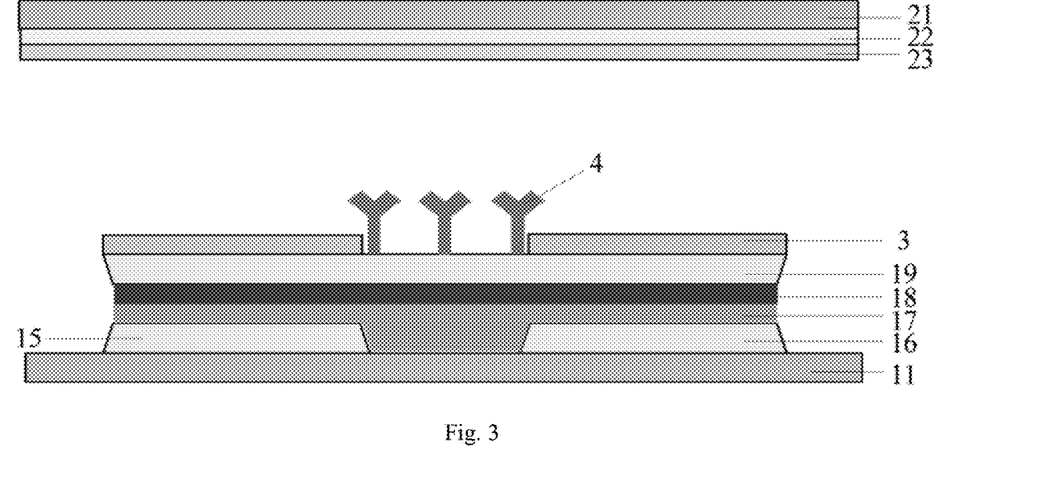
FIG. 3 is a schematic sectional view of a microfluidic structure in a detection area provided by an embodiment of the present disclosure.

As shown in FIG. 1 being a schematic top view of a microfluidic structure, FIG. 2 being a schematic diagram of a sectional structure of a microfluidic structure in channel areas and FIG. 3 being a schematic diagram of a sectional structure of the microfluidic structure in a detection area, an embodiment of the present disclosure provides a microfluidic structure, including: a first base substrate 11 and a second base substrate 21 opposite to each other, an antibody area located between the first base substrate 11 and the second base substrate 21 and storing an enzyme-labeled first antibody, a cleaning area storing cleaning liquid, a signal substrate area storing a signal substrate solution and a detection area with a second antibody 4 and an ion sensitive film 3 fixed thereon. The enzyme-labeled first antibody includes a first antibody and an enzyme attached to the first antibody. The first antibody is an antibody matched with a to-be-detected antigen. The second antibody is an antibody matched with the first antibody.

All channel areas 10 from the antibody area, the cleaning area and the signal substrate area to the detection area each have a driving electrode structure driving liquid drops to move, namely, the channel area 10 from the antibody area to the detection area has the driving electrode structure, the channel area 10 from the cleaning area to the detection area has the driving electrode structure, and the channel area 10 from the signal substrate area to the detection area has the driving electrode structure.

The detection area has a thin film transistor connected with the ion sensitive film 3.

According to the microfluidic structure provided by the embodiment of the present disclosure, when the to-be-detected antigen needs to be detected, the antigen may be combined with the enzyme-labeled first antibody in the antibody area to form antigen/enzyme-labeled antibody mixed liquid drops, then a voltage is sequentially loaded to the driving electrode structure from the antibody area to the detection area, so that the antigen/enzyme-labeled antibody mixed liquid drops are moved from the antibody area to the detection area, and the antigen/enzyme-labeled antibody mixed liquid drops are combined with the second antibody in the detection area to form antigen/antibody sandwich composite liquid drops. After reaction for a first duration, a voltage is sequentially loaded to the driving electrode structure from the cleaning area to the detection area, so that cleaning liquid drops in the cleaning area are moved to the detection area to take away a non-combined reactant. After reaction for a second duration, a voltage is sequentially loaded to the driving electrode structure from the signal substrate area to the detection area, so that signal substrate liquid drops in the signal substrate area are moved to the detection area, and a signal substrate forms ions under the action of the enzyme. The ion sensitive film produces inductive charges under the action of the ions, thus an electrical signal output by the thin film transistor changes, and then according to the change of the electrical signal of the thin film transistor, a content of the to-be-detected antigen may be determined. The microfluidic structure does not need an external optical system and a magnetic control module, the quantity of consumed reagent is small, and the cost is low. Besides, microfluidic high-accuracy liquid drop control may improve a variable coefficient difference value in a batch or between batches. Moreover, a microfluidic integrated detection structure facilitates miniaturization and portability of a detection apparatus, and point-of-care testing (POCT) of detection of the antigen including cardiac markers and the like is achieved.

Figure 4:
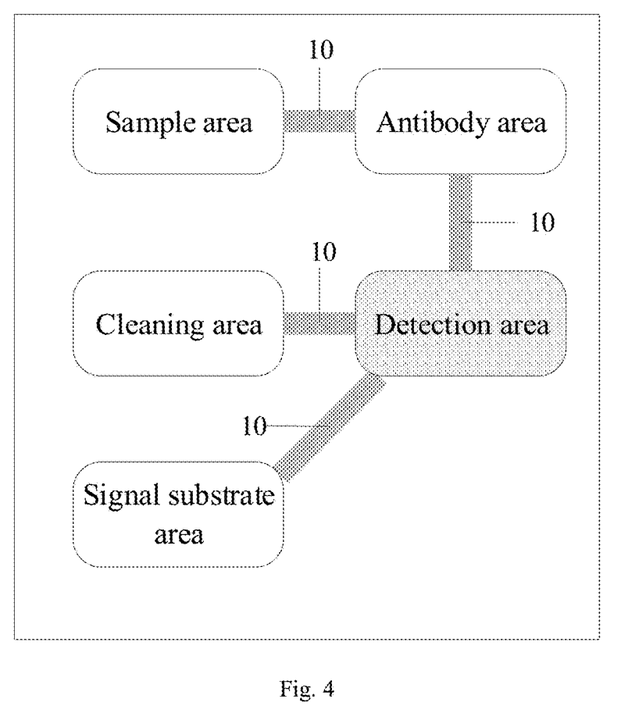
FIG. 4 is a schematic top view of a microfluidic structure including a sample area provided by an embodiment of the present disclosure.

In some embodiments, a liquid inlet may be formed between the antibody area and the outside, and the to-be-detected antigen may directly enter the antibody area through the liquid inlet. In some embodiments, in order to accurately control the quantity of the antigen entering the antibody area, a sample area may be further arranged on the microfluidic structure. As shown in FIG. 4, the microfluidic structure further includes: the sample area located between the first base substrate 11 and the second base substrate 21 and storing the to-be-detected antigen. A channel area 10 from the sample area to the detection area also has a driving electrode structure driving liquid drops to move. The driving electrode structure from the sample area to the detection area may be the same as the driving electrode structure from the antibody area to the detection area. In some embodiments, the sample area may store a to-be-detected sample solution, and the to-be-detected sample solution may include the to-be-detected antigen such as cardiac markers. When the microfluidic structure further includes the sample area, the liquid inlet may be formed between the sample area and the outside, namely, the to-be-detected antigen may enter the sample area and then enter the antibody area. A content of the antigen entering the detection area may be controlled by controlling the loaded voltages of the driving electrode structures or coverage of the loaded voltages of the driving electrode structures.

Figure 5:
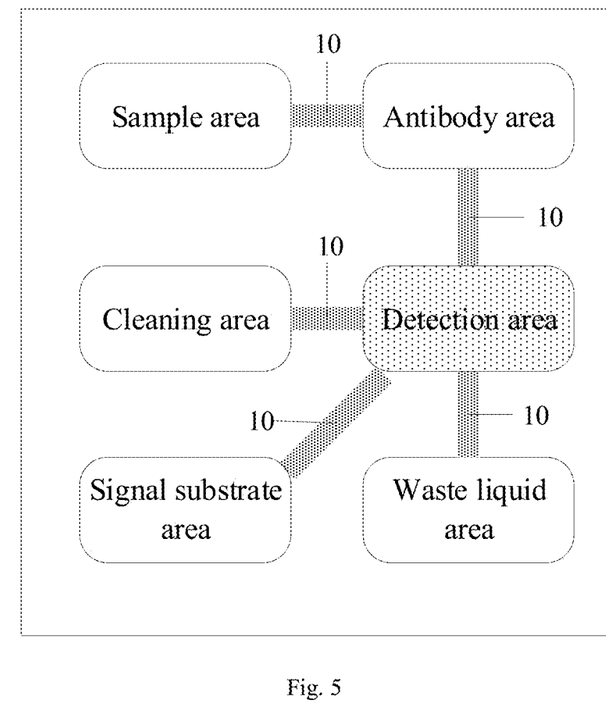
FIG. 5 is a schematic top view of a microfluidic structure including a waste liquid area provided by an embodiment of the present disclosure.

In some embodiments, as shown in FIG. 5, the microfluidic structure further includes: a waste liquid area located between the first base substrate 11 and the second base substrate 21. A channel area 10 from the detection area to the waste liquid area also has a driving electrode structure driving liquid drops to move. In the embodiment of the present disclosure, the microfluidic structure further includes the waste liquid area so that a non-reacted reactant can be discharged in time after a reaction of a reactant in the detection area is completed. Certainly, a liquid outlet may be formed so that the reactant finishing the reaction can be discharged out of the microfluidic structure.

In some embodiments, as shown in FIG. 3, the ion sensitive film 3 and the second antibody 4 are located on the same layer. The ion sensitive film 3 has a hollow-out area, and the second antibody 4 is located in the hollow-out area. In the embodiment of the present disclosure, the ion sensitive film 3 and the second antibody 4 are located on the same layer so that the second antibody 4 can react with the antigen/enzyme-labeled antibody mixed liquid drops, the ion sensitive film 3 can make contact with subsequent survival ions, then inductive charges are produced, and an electric potential of a gate electrode of the thin film transistor is affected.

In some embodiments, as shown in FIG. 3, the thin film transistor includes a source electrode 15 and a drain electrode 16 located on the first base substrate 11, an active layer 17 located on one face of the source electrode 15 and one face of the drain electrode 16 facing the second base substrate 21, a gate electrode insulation layer 18 located on one face of the active layer 17 facing the second base substrate 21 and a gate electrode 19 located on one face of the gate electrode insulation layer 18 facing the second base substrate 21. The ion sensitive film 3 covers one face of the gate electrode 19 facing the second base substrate 21. In the embodiment of the present disclosure, the thin film transistor is a top gate electrode type thin film transistor, namely, the ion sensitive film 3 makes contact with the gate electrode 19 of the thin film transistor. The ion sensitive film 3 produces inductive charges under the action of the ions generated after the enzyme reacts with the signal substrate, thus the electric potential of the gate electrode 19 of the thin film transistor may be affected directly, change of the electric potential of the gate electrode 19 may result in change of a conductive characteristic of the active layer 17 of a semiconductor, thus an electric current may be generated between the source electrode 15 and the drain electrode 16, and then the content of the to-be-detected antigen may be determined by detecting an electric current signal between the source electrode 15 and the drain electrode 16 of the transistor. Specifically, a plurality of thin film transistors may be arranged in the detection area, an arrangement mode of the plurality of thin film transistors may be similar with that of thin film transistors in a display panel, namely, gate electrodes of the thin film transistors on the same row are connected to one gate electrode line, source electrodes of the thin film transistors on the same column are connected to one data line, independent control over each of the thin film transistors may be achieved through the gate electrode line and control over an electric potential of the data line.

In some embodiments, the driving electrode structures may be arranged only in all the channel areas 10 of the first base substrate 11 and the second base substrate 21. Or all the channel areas 10 of the first base substrate 11 and the second base substrate 21, the sample area, the antibody area, the cleaning area, the signal substrate area and the waste liquid area each have the driving electrode structure. Or the driving electrode structures may be arranged in all of the other areas of the first base substrate 11 and the second base substrate 21 except for the detection area. During specific implementation, as shown in FIG. 2, each of the driving electrode structures includes a plurality of first electrodes 12 located on the first base substrate 11 at intervals, and a common electrode 22 located on the second base substrate 21. Specifically, the first electrodes 12 may be distributed in an array mode in each area, and the common electrode 22 may be of a whole surface structure for all the areas.

In some embodiments, each of the channel areas 10 further includes a first hydrophobic layer 13 located on one face of the first electrodes 12 facing the second base substrate 21 and a second hydrophobic layer 23 located on one face of the common electrode 22 facing the first base substrate 11. Specifically, each of the channel areas 10 further includes a dielectric layer 14 located between the first electrodes 12 and the first hydrophobic layer 13.

In some embodiments, the enzyme in the enzyme-labeled first antibody may include: alkaline phosphatase or horse radish peroxidase. The signal substrate may include phospholipid aminobenzoate or 2-phosphate ascorbate.

On the basis of the same inventive concept, an embodiment of the present disclosure further provides a microfluidic chip, including a plurality of microfluidic structures provided by the embodiment of the present disclosure. In the embodiment of the present disclosure, one microfluidic chip may integrate a plurality of microfluidic structures provided by the embodiment of the present disclosure. Namely, detection of different cardiac markers of the same sample may be performed on the chip at the same time, detection of the same cardiac marker of different samples may be performed on the chip, and thus multi joint detection of the cardiac markers is achieved.

Figure 6:
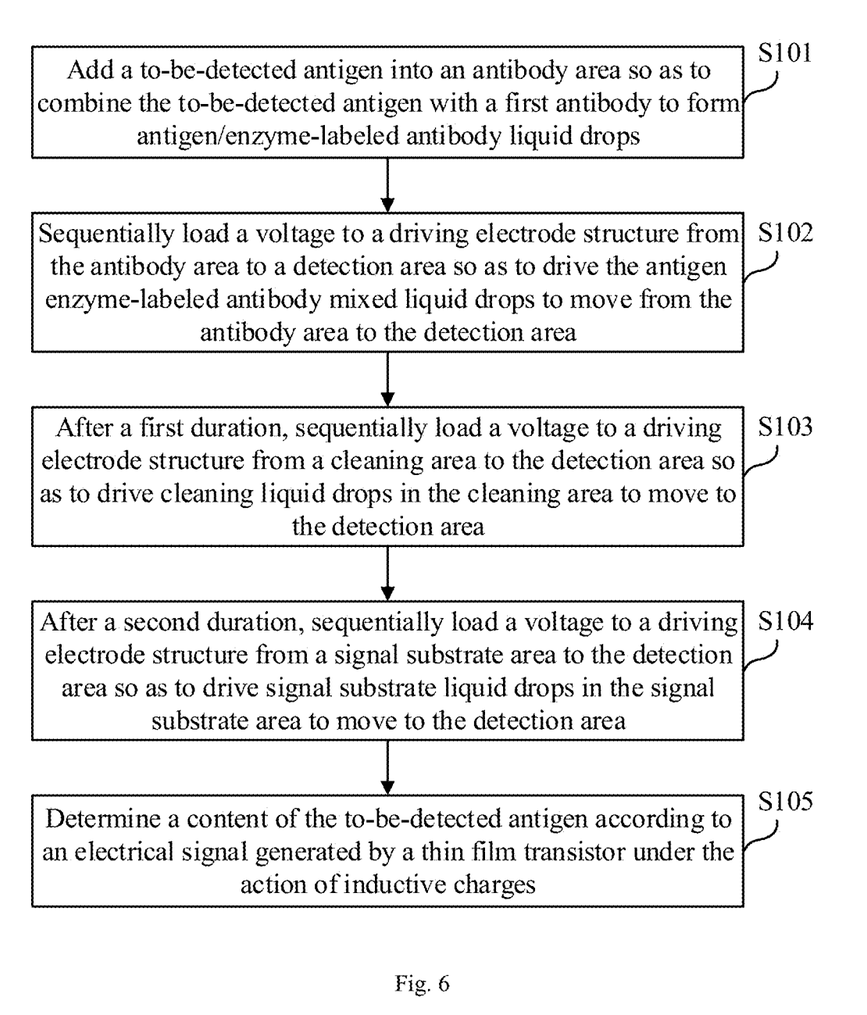
FIG. 6 is a flow chart of detection of a microfluidic structure provided by an embodiment of the present disclosure.

On the basis of the same inventive concept, an embodiment of the present disclosure further provides a detection method driving the microfluidic structure provided by the embodiment of the present disclosure, as shown in FIG. 6, including: S101-S105.

S101, a to-be-detected antigen is added into an antibody area so that the to-be-detected antigen is combined with an enzyme-labeled first antibody to form antigen/enzyme-labeled antibody mixed liquid drops.

S102, a voltage is sequentially loaded to a driving electrode structure from the antibody area to a detection area, so that the antigen/enzyme-labeled antibody mixed liquid drops are driven to move from the antibody area to the detection area, and then the antigen/enzyme-labeled antibody mixed liquid drops are combined with a second antibody to form antigen/antibody sandwich composite liquid drops.

S103, after a first duration, a voltage is sequentially loaded to a driving electrode structure from a cleaning area to the detection area, so that cleaning liquid drops in the cleaning area are driven to move to the detection area to take away a non-combined reactant.

S104, after a second duration, a voltage is sequentially loaded to a driving electrode structure from a signal substrate area to the detection area, so that signal substrate liquid drops in the signal substrate area are driven to move to the detection area, then a signal substrate forms ions under the action of the enzyme, and an ion sensitive film produces inductive chargers under the action of the ions.

S105, according to an electrical signal generated by a thin film transistor under the action of the inductive charges, a content of the to-be-detected antigen is determined.

In some embodiments, the microfluidic structure may further include a sample area, and thus S101, namely adding the to-be-detected antigen to the antibody area, includes: S1011-S1012.

S1011, the to-be-detected antigen is added into the sample area.

S1012, a voltage is sequentially loaded to a driving electrode structure from the sample area to the antibody area, so that liquid drops containing the to-be-detected antigen in the sample area are driven to move to the antibody area.

During specific implementation, the microfluidic structure may further include a waste liquid area, and thus before S104, namely before sequentially loading the voltage to the driving electrode structure from the signal substrate area to the detection area, the detection method further includes:

S106, a voltage is sequentially loaded to a driving electrode structure from the detection area to the waste liquid area, so that the non-combined reactant is driven to move to the waste liquid area.

Figure 7:
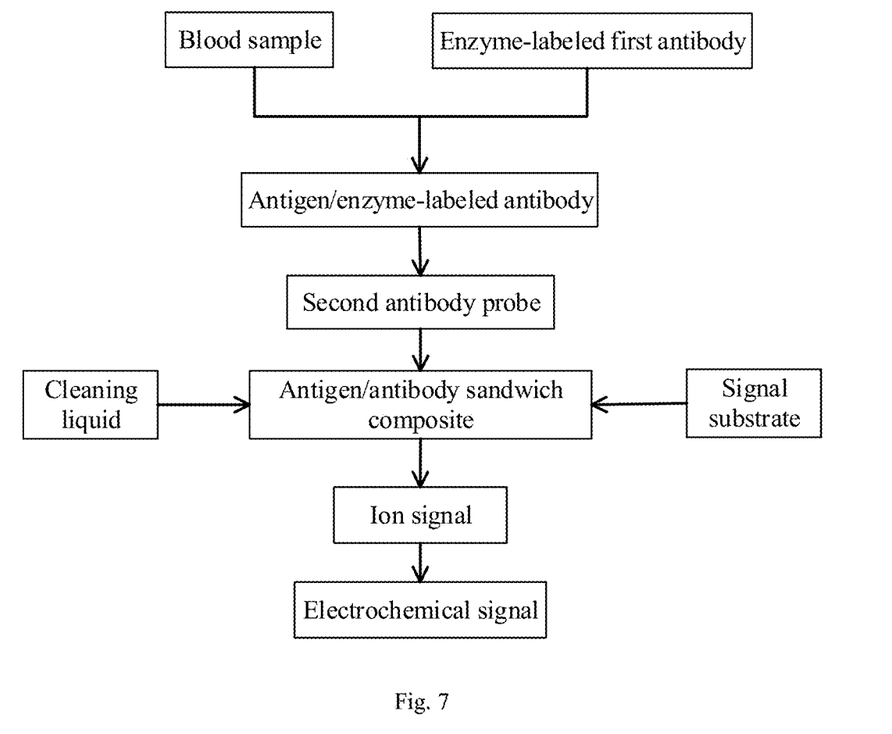
FIG. 7 is a specific flow chart of detection of a microfluidic structure provided by an embodiment of the present disclosure.
Figure 8:
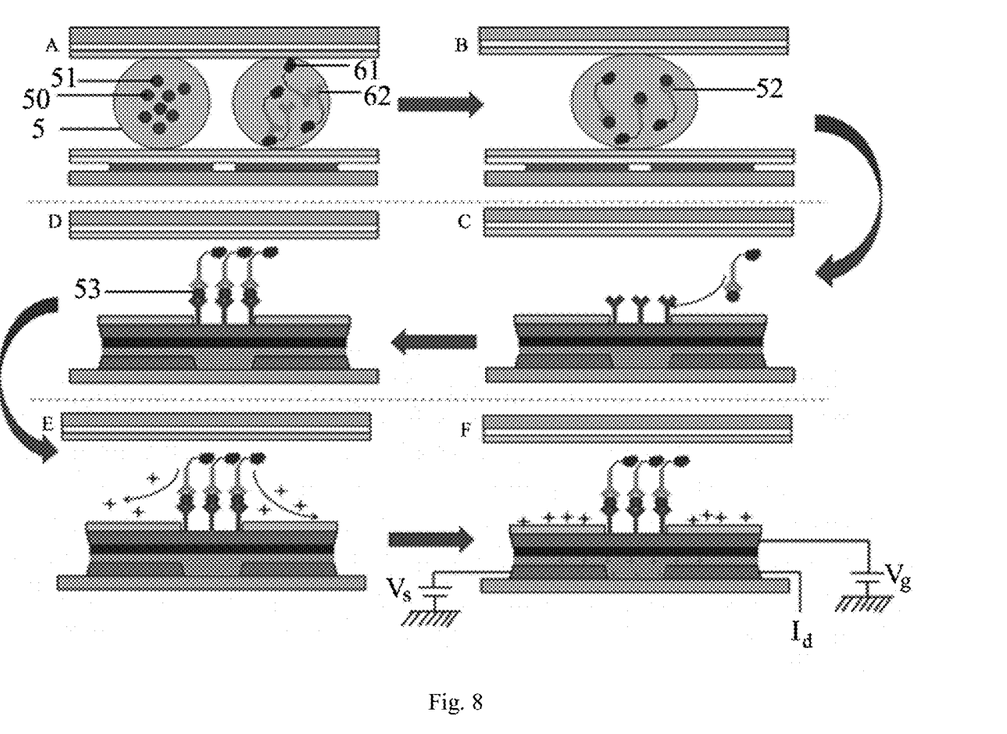
FIG. 8 is another specific flow chart of detection of a microfluidic structure provided by an embodiment of the present disclosure.

In order to more clearly understand a detection principle of the microfluidic structure provided by the embodiment of the present disclosure, a microfluidic detection structure and a detection process provided by an embodiment of the present disclosure are further described in details as follows in combination with the FIG. 2, FIG. 3, FIG. 5. FIG. 7 and FIG. 8.

As for the microfluidic structure.

As shown in FIG. 5: the microfluidic structure for detection of cardiac markers mainly includes six function areas: a sample area, an antibody area, a cleaning area, a signal substrate area, a waste liquid area and a detection area. The sample area is a to-be-detected sample solution storage area. The antibody area is an enzyme-labeled first antibody reaction liquid storage area. The cleaning area provides cleaning liquid for a reaction. The signal substrate area is a signal substrate solution storage area. The waste liquid area collects waste liquid generated by the reaction in the microfluidic structure. The detection area is for capturing a marked sample and serving as a signal substrate to produce a signal with the sample. The adopted microfluidic structure is a double-base-plate structure, an upper base substrate is a substrate base substrate (namely, a second base substrate 21, being glass, silicon base, plastics, etc.), a grounded metal electrode (namely, a common electrode 22, like an ITO conductive layer, etc.) and a second hydrophobic layer 23 (like Teflon, etc.) from top to bottom in sequence. A lower base substrate includes a substrate base substrate (namely, a first base substrate 11), a metal electrode (namely, a first electrode 12), a dielectric layer 14 and a hydrophobic layer 13 from bottom to top. The sample area, the antibody area, the cleaning area, the signal substrate area, the waste liquid area and all channel areas are each composed of these structures and are mutually connected, and electrodes are powered on so as to achieve separation, movement, fusion and the like of liquid drops. As for the detection area, the upper base substrate of the detection area is the same as that of the upper base substrate of other areas, and the lower base substrate is of a top gate electrode TFT structure (a gate electrode being at the top). A layer of ion sensitive film 3 is deposited on the surface of a gate electrode 19, an insulation layer 18 is located below the gate electrode 19, an a-Si semiconductor material (namely, an active layer 17) is deposited below the insulation layer 18 and is together with a source electrode 15 and a drain electrode 16 on the two sides to form a top gate electrode structure. A second antibody 4 is modified on the gate electrode 19 to form a probe for capturing a target molecule.

As for the detection process.

As shown in FIG. 7 and FIG. 8, the cardiac markers in to-be-detected sample liquid drops are mixed with an antibody of an enzyme-labeled (like alkaline phosphatase and horse radish peroxidase) first antibody in a microfluidic chip (in FIG. 8A, including to-be-detected liquid drops 5 located on the left side and containing the to-be-detected antigen 51 and other antigens 50 and the enzyme-labeled first antibody located on the right side and containing an enzyme 61-labeled first antibody 61), and antigen/enzyme-labeled antibody mixed liquid drops 52 are formed (FIG. 8B). The antigen/enzyme-labeled antibody mixed liquid drops 52 are moved to the detection area (FIG. 8C). The antigen/enzyme-labeled antibody mixed liquid drops 52 are captured by the second antibody 4, and antigen/antibody sandwich composite liquid drops 53 are formed (FIG. 8D). A non-captured composite is washed away by feeding washing liquid, residues are prevented, and then the signal substrate (like phospholipid aminobenzoate, 2-phosphate ascorbate, etc.) is added. Under enzyme catalysis action on the antigen/antibody sandwich composite liquid drops 53, the signal substrate forms ions (like phosphate ions, hydrogen ions, etc., FIG. 8E) captured by the ion sensitive film 3 on the gate electrode 19, corresponding charges are induced on the surface of the ion sensitive film 3, thus an electric potential of the gate electrode 19 below is increased, a conductive characteristic of the a-si semiconductor active layer below changes, at the moment, an electric current between the source electrode and the drain electrode changes (FIG. 8F), and a concentration of the cardiac markers is detected by detecting change of the electric current.

The embodiments of the present disclosure have the beneficial effects as follows: according to the microfluidic structure provided by the embodiment of the present disclosure, when the to-be-detected antigen needs to be detected, the antigen may be combined with the enzyme-labeled first antibody in the antibody area to form antigen/enzyme-labeled antibody mixed liquid drops, then the voltage is sequentially loaded to the driving electrode structure from the antibody area to the detection area so as to make the antigen/enzyme-labeled antibody mixed liquid drops move from the antibody area to the detection area, and thus the antigen/enzyme-labeled antibody mixed liquid drops are combined with the second antibody in the detection area to form antigen/antibody sandwich composite liquid drops. After reaction for the first duration, the voltage is sequentially loaded to the driving electrode structure from the cleaning area to the detection area, so that the cleaning liquid drops in the cleaning area are moved to the detection area to take away the non-combined reactant. After reaction for the second duration, the voltage is sequentially loaded to the driving electrode structure from the signal substrate area to the detection area, so that the signal substrate liquid drops in the signal substrate area are moved to the detection area, the signal substrate forms the ions under the action of the enzyme, the ion sensitive film produces the inductive charges under the action of the ions, then an electrical signal output by the thin film transistor changes, and according to change of the electrical signal of the thin film transistor, the content of the to-be-detected antigen may be determined. The microfluidic structure does not need the external optical system and the magnetic control module, the quantity of consumed reagent is small, and the cost is low. Besides, microfluidic high-accuracy liquid drop control may improve the variable coefficient difference value in the batch or between the batches. Moreover, the microfluidic integrated detection structure facilitates miniaturization and portability of the detection apparatus, and point-of-care testing (POCT) of detection of the antigen including the cardiac markers and the like is achieved.

Apparently, those skilled in the part may make various changes and transformations for the present disclosure without departing from the spirit and the scope of the present disclosure. In this case, if these changes and transformations of the present disclosure fall in the scope of claims and the equivalent art thereof, the present disclosure intends to include these changes and transformations.

What is claimed is:
1. A microfluidic structure, comprising:
 a first base substrate and a second base substrate opposite to each other;
 an antibody area located between the first base substrate and the second base substrate and storing an enzyme-labeled first antibody;
 a cleaning area storing cleaning liquid;
 a signal substrate area storing a signal substrate solution; and
 a detection area with a second antibody and an ion sensitive film fixed thereon; wherein
 the enzyme-labeled first antibody comprises a first antibody and an enzyme attached to the first antibody, wherein the first antibody is an antibody matched with a to-be-detected antigen, and the second antibody is an antibody matched with the first antibody;
 all channel areas from the antibody area, the cleaning area and the signal substrate area to the detection area each have a driving electrode structure driving liquid drops to move; and
 the detection area has a thin film transistor connected with the ion sensitive film.

2. The microfluidic structure according to claim 1, wherein the ion sensitive film and the second antibody are located on a same layer; and
 the ion sensitive film has a hollow-out area, and the second antibody is located in the hollow-out area.

3. The microfluidic structure according to claim 2, wherein the thin film transistor comprises:
 a source electrode and a drain electrode located on the first base substrate;
 an active layer located on one face of the source electrode and one face of the drain electrode facing the second base substrate;
 a gate electrode insulation layer located on one face of the active layer facing the second base substrate; and
 a gate electrode located on one face of the gate electrode insulation layer facing the second base substrate; wherein
 the ion sensitive film covers one face of the gate electrode facing the second base substrate.

4. The microfluidic structure according to claim 1, wherein the driving electrode structure comprises:
 a plurality of first electrodes located on the first base substrate at intervals; and
 a common electrode located on the second base substrate.

5. The microfluidic structure according to claim 4, wherein each of the channel areas further comprises:
 a first hydrophobic layer located on one face of the first electrodes facing the second base substrate; and
 a second hydrophobic layer located on one face of the common electrode facing the first base substrate.

6. The microfluidic structure according to claim 5, wherein the each of the channel areas further comprises a dielectric layer located between the first electrodes and the first hydrophobic layer.

7. The microfluidic structure according to claim 1, further comprising:
 a sample area located between the first base substrate and the second base substrate and storing the to-be-detected antigen; wherein
 a channel area from the sample area to the detection area has a driving electrode structure driving liquid drops to move.

8. The microfluidic structure according to claim 7, further comprising:
 a waste liquid area located between the first base substrate and the second base substrate; wherein a channel area from the detection area to the waste liquid area has a driving electrode structure driving liquid drops to move.

9. The microfluidic structure according to claim 1, wherein the enzyme comprises: alkaline phosphatase or horse radish peroxidase.

10. The microfluidic structure according to claim 9, wherein a signal substrate comprises: phospholipid aminobenzoate or 2-phosphate ascorbate.

11. A microfluidic chip, comprising a plurality of microfluidic structures, wherein each of the microfluidic structures comprises:
   a first base substrate and a second base substrate opposite to each other;
   an antibody area located between the first base substrate and the second base substrate and storing an enzyme-labeled first antibody;
   a cleaning area storing cleaning liquid;
   a signal substrate area storing a signal substrate solution; and
   a detection area with a second antibody and an ion sensitive film fixed thereon; wherein
   the enzyme-labeled first antibody comprises a first antibody and an enzyme attached to the first antibody, wherein the first antibody is an antibody matched with a to-be-detected antigen, and the second antibody is an antibody matched with the first antibody;
   all channel areas from the antibody area, the cleaning area and the signal substrate area to the detection area each have a driving electrode structure driving liquid drops to move; and
   the detection area has a thin film transistor connected with the ion sensitive film.

12. A detection method for detection by adopting the microfluidic structure according to claim 1, comprising:
   combining the to-be-detected antigen with the enzyme-labeled first antibody to form antigen/enzyme-labeled antibody mixed liquid drops by adding the to-be-detected antigen into the antibody area;
   driving the antigen/enzyme-labeled antibody mixed liquid drops to move from the antibody area to the detection area by sequentially loading a voltage to the driving electrode structure from the antibody area to the detection area, and forming antigen/antibody sandwich composite liquid drops by combining the antigen/enzyme-labeled antibody mixed liquid drops with the second antibody;
   after a first duration, driving cleaning liquid drops in the cleaning area to move to the detection area to take away a non-combined reactant by sequentially loading a voltage to the driving electrode structure from the cleaning area to the detection area;
   after a second duration, driving signal substrate liquid drops in the signal substrate area to move to the detection area and make a signal substrate form ions under the action of the enzyme and make the ion sensitive film produce inductive charges under the action of the ions by sequentially loading a voltage to the driving electrode structure from the signal substrate area to the detection area; and
   determining a content of the to-be-detected antigen according to an electrical signal generated by the thin film transistor under the action of the inductive charges.

13. The detection method according to claim 12, wherein adding the to-be-detected antigen into the antibody area comprises:
   adding the to-be-detected antigen into a sample area; and
   driving liquid drops containing the to-be-detected antigen in the sample area to move to the antibody area by sequentially loading a voltage to the driving electrode structure from the sample area to the antibody area.

14. The detection method according to claim 13, wherein before sequentially loading the voltage to the driving electrode structure from the signal substrate area to the detection area, the detection method further comprises:
   driving the non-combined reactant to move to a waste liquid area by sequentially loading a voltage to the driving electrode structure from the detection area to the waste liquid area.

* * * * *